US006402961B1

(12) United States Patent
Bade et al.

(10) Patent No.: US 6,402,961 B1
(45) Date of Patent: Jun. 11, 2002

(54) PROCESS FOR PREPARING EPOXYSILANES

(75) Inventors: Stefan Bade; Uwe Schoen; Hartwig Rauleder, all of Rheinfelden (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/621,076

(22) Filed: Jul. 21, 2000

(30) Foreign Application Priority Data

Jul. 23, 1999 (DE) .......................... 199 34 576

(51) Int. Cl.$^7$ .............................. B01D 15/08
(52) U.S. Cl. ................ 210/679; 502/405; 502/415; 502/416; 549/215; 556/479; 203/41
(58) Field of Search .................. 210/679; 502/415, 502/416, 405; 556/479; 549/215; 203/41

(56) References Cited

U.S. PATENT DOCUMENTS 4,900,520 A * 2/1990 Behnam et al.
5,115,069 A * 5/1992 Motegi et al.
5,248,751 A * 9/1993 Takahashi et al. .......... 524/265
5,368,048 A * 11/1994 Stoy et al. .................. 156/86
5,567,833 A * 10/1996 Iwahara et al.
6,100,408 A * 8/2000 Monkiewicz et al.

FOREIGN PATENT DOCUMENTS

| DE | 0 262 642 | 4/1988 |
| DE | 0 277 023 | 8/1988 |
| DE | 0 288 286 | 10/1988 |
| DE | 198 05 083 | 8/1999 |
| EP | 0 548 974 | 6/1993 |
| JP | 05-179246 A * | 7/1993 |

* cited by examiner

Primary Examiner—Robert Dawson
Assistant Examiner—Marc S. Zimmer
(74) Attorney, Agent, or Firm—Oblon, Spivak, McClelland, Maier & Neustadt, P.C.

(57) ABSTRACT

A process for preparing epoxysilanes by reacting a hydrogensilane with an allyl glycidyl ether in the presence of a catalyst and working up the crude product obtained, where the catalyst is removed from the crude product and the crude product is subsequently distilled.

15 Claims, No Drawings

PROCESS FOR PREPARING EPOXYSILANES

BACKGROUND OF THE INVENTION

1. Field of the Invention

The present invention relates to a process for preparing epoxysilanes by reacting a hydrogensilane with an allyl glycidyl ether in the presence of a catalyst followed by purification.

2. Background of the Invention

The preparation of epoxysilanes by reacting hydrogensilanes with allyl glycidyl ether in the presence of a hydrosilylation catalyst based on Pt(0) is described in the German patent application 198 05 083.6. However, other catalyst systems can in principle also be used for hydrosilylation reactions, for example simple compounds or complexes of nickel, platinum, rhodium or ruthenium in their various oxidation states, cf., for example, EP 0 262 642 A2, EP 0277023 A2, EP 0288286 A2 and EP 0548 974 A1.

It is also known that, for example, in the reaction of allyl glycidyl ether with trimethoxysilane,

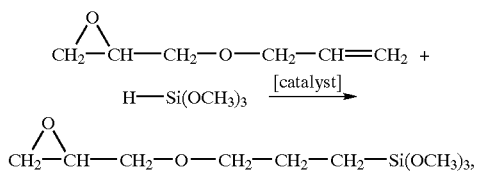

the resulting crude product contains not only 3-glycidyloxypropyltrimethoxysilane (GLYMO)

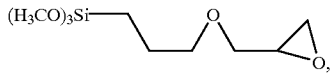

but also unreacted starting materials, isomerized allyl glycidyl ether, isomerized epoxysilane, viz. 2-glycidyloxy-1-methylethyltrimethoxysilane (iso-GLYMO)

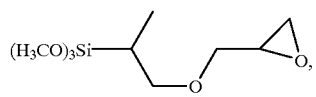

tetraalkoxysilane and "cyclic alkoxysilane" formed by cyclization of epoxysilanes, viz 1-dimethoxysila-2,5-dioxa-3-methoxymethylcyclooctane (cyclo-GLYMO)

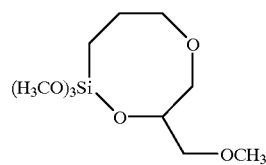

but also the catalyst used.

The crude product is customarily worked up by means of column distillation. The work-up is generally very complicated and time-consuming. Furthermore, it is found that additional amounts of the "cyclized alkoxysilane" (cyclo-GLYMO) are continually formed during the distillative work-up.

Since there is only a small difference in the boiling points of the target product "epoxysilane" and the "cyclized epoxysilane", the running time of a batch distillation is increased significantly and quantitative removal of the "cyclized epoxysilane" by means of column distillation is not possible on an industrial scale. However, quantitative separation of the "cyclized epoxysilane" from the main product is necessary to achieve very high epoxysilane purities. In addition, a high proportion of undesirable high boilers, which reduces the yield of epoxysilane, is formed under the conditions prevailing in the distillation.

SUMMARY OF THE INVENTION

It is therefore an object of the invention to provide a process for preparing epoxysilanes which avoids the disadvantages discussed above, where possible.

It has surprisingly been found that the abovementioned disadvantages can be avoided if the work-up of the crude epoxysilane product is carried out in two steps, with the catalyst still present in the crude product obtained directly from the epoxysilane synthesis being removed from the crude product in a first step and the crude product mixture which has been essentially freed of catalyst being subjected to a work-up by distillation in a second step.

Thus, the present invention provides a process for preparing an epoxysilane, comprising:

reacting a hydrogensilane with an allyl glycidyl ether in the presence of a catalyst to form a crude product, removing the catalyst from the crude product, and then distilling the crude product.

The work-up by distillation of the essentially catalyst-free crude product is preferably carried out by means of column distillation. The removal of the hydrosilylation catalyst from the crude epoxysilane product is preferably carried out by adsorption or by reduction. The present process provides epoxysilanes having high purities.

A more complete appreciation of the invention and many of the attendant advantages thereof will be readily obtained as the same becomes better understood by reference to the following detailed description.

DETAILED DESCRIPTION OF THE INVENTION

In the process of the invention, the hydrogensilane component used can be, for example, trimethoxysilane, triethoxysilane, methyldimethoxysilane, methyldiethoxysilane, tri-n-propoxysilane, tri-n-butoxysilane, triisopropoxysilane, methyldi-n-propoxysilane, methyldiisopropooxysilane, methyldi-n-butoxysilane, triisobutoxysilane, methyldiisobutoxysilane, phenyldimethoxysilane, phenyldiethoxysilane, phenyldi-n-propoxysilane, phenyldiisopropoxysilane, phenyldi-n-butoxysilane or phenyldiisobutoxysilane. Mixtures of these hydrogensilanes may be used.

In the process of the invention, the preferred epoxysilanes are represented by the general formula I:

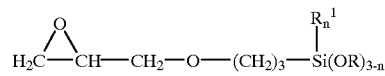

where

R is a linear or branched alkyl group having from 1 to 4 carbon atoms or an aryl group having from 6 to 12 carbon atoms, $R^1$ is a linear or branched alkyl group having from 1 to 4 carbon atoms, and n is 0 or 1 or 2.

Examples of these epoxysilanes include 3-glycidyloxypropyltrimethoxysilane (GLYMO), 3-glycidyloxypropyltriethoxysilane (GLYEO), 3-glycidyloxypropyltri-n-propoxysilane, 3-glycidyloxypropyltriisopropoxysilane, 3-glycidyloxypropyltrin-butoxysilane, and 3-glycidyloxypropyltriisobutoxysilane.

The hydrosilylation catalyst used in the process of the invention is preferably a noble metal catalyst based on Pt, Pd, Rh or Ir.

The hydrosilylation reaction may be conducted under conditions which are known per se. Then, according to the invention, the catalyst is removed from the product obtained, generally to concentrations of <10 mg/kg, calculated as noble metal, and the essentially catalyst-free crude product is worked up by distillation, for example by means of column distillation.

The catalyst is preferably removed from the crude product by adsorption. The adsorption is advantageously carried out in a fixed absorber bed. However, it is also possible to add a solid absorber to the crude product to be treated and subsequently separate it off by filtration or by means of another liquid/solid separation process.

Preference is given to using adsorbers having a mean particle size of from 1 to 30 mm, particularly preferably from 5 to 20 mm. These ranges include all specific values and subranges therebetween, such as 2, 8, 10, 12, 15 and 25 mm. The adsorbers used in the process of the invention generally have an internal surface area of from 10 to 1500 $m^2/g$. These ranges include all specific values and subranges therebetween, such as 25, 50, 100, 250, 500 and 1000 $m^2/g$.

In particular, it is possible to use activated carbon, silica, for example pyrogenic or precipitated silica, aluminum oxide, titanium dioxide, zirconium oxide or zeolites or else polymeric resins as adsorbers. However, it is also possible to use other materials which are suitable as adsorbers. In the present process, it is also possible to use a mixture of solid adsorbers. It is advantageous to use neutral adsorbers. Furthermore, the absorbents used in the process of the present invention should be essentially free of water.

In the process of the invention, preference is given to using adsorbers having an internal surface area (BET) of from 150 to 1400 $m^2/g$, more preferably from 600 to 1400 $m^2/g$, even more preferably from 1000 to 1500 $m^2/g$. These ranges include all specific values and subranges therebetween, such as 250, 500, 750 and 1200 $m^2/g$.

In the process of the invention, the adsorption is preferably carried out at a temperature in the range from 0 to 120° C., particularly preferably at a temperature in the range from 10 to 50° C., very particularly preferably at a temperature in the range from 10 to 25° C. These ranges include all specific values and subranges therebetween, such as 20, 30, 60, 80 and 100° C.

The work-up according to the invention of the said crude product can be carried out under reduced pressure. The adsorption in the process of the invention is preferably carried out at a pressure in the range from 0.5 to 5 bar abs. (absolute), particularly preferably from 0.7 to 2 bar abs. (absolute), very particularly preferably from 1.0 to 1.5 bar abs. (absolute).

The residence time of the crude product in the absorber bed or over the adsorbent is preferably from 5 minutes to 2 hours; preference is given to a contact time of from 10 to 60 minutes. The time is particularly preferably from 15 to 45 minutes.

In the process of the invention, the catalyst can also be precipitated from the crude product by reduction and thus be removed from the crude product. Examples of reducing agents which can be used are metallic zinc in the form of powder or of pieces which can easily be removed from the crude product again.

The inventive process provides the following advantages:

achievement of particularly high epoxysilane purities, in particular $\geq 99\%$, in the work-up by distillation, because the further formation of the "cyclized epoxysilane" (="cyclic alkoxysilane") is very substantially suppressed during the distillation.

shortening of the intermediate fraction in the work-up by distillation and thus an increase in the distillation capacity, a low proportion of high boilers which are formed during the distillation and thus an increase in the yield of epoxysilane in the distillation, the adsorbed noble metal catalyst can be worked up to recover the noble metal.

no epoxysilane losses as would occur in the work-up of the crude epoxysilane mixture by means of a thin-film evaporator, no addition of auxiliaries to deactivate the catalyst is necessary, and low energy consumption and technical simplicity in removal of catalyst by adsorption.

EXAMPLES

Having generally described this invention, a further understanding can be obtained by reference to certain specific examples which are provided herein for purposes of illustration only and are not intended to be limiting unless otherwise specified.

Example 1

Crude GLYMO product having a Pt content of 12 ppm is passed at 20° C. over an absorber bed comprising granulated activated carbon having a mean diameter of 1.5 mm. The front-end pressure at the absorber bed is 1.1 bar abs. The adsorber bed occupies a volume of 100 $cm^3$, the mass of the activated carbon is 50.0 g and the void volume is about 60%. The dimensions of the adsorber bed are: internal diameter 22 mm, length 320 mm. At a volume flow of 200 standard ml/h of epoxysilane and thus a residence time of 39 minutes in the adsorber bed, a Pt content of 2 ppm is found in the eluate. The Pt content of the epoxysilane is thus reduced by 84%. According to GC analysis, the epoxysilane experiences no change over the adsorber bed.

The work-up of the adsorptively purified crude epoxysilane product by distillation in a batch distillation column resulted in an epoxysilane purity of 99.4%. Under the same boundary conditions, it was only possible to achieve a purity of 98.6% using a crude epoxysilane product which had not been purified by adsorption. The mass balance of the individual fractions indicated that the undesired cyclized epoxysilane is formed during the distillation only when the crude epoxysilane has not been purified by adsorption and the catalyst is present during the distillation. In contrast, if the epoxysilane is purified by adsorption prior to the distillation, there is no further formation of cyclized epoxysilane during the distillation.

Example 2

Crude GLYMO product having a Pt content of 12 ppm is passed at 20° C. over an adsorber bed comprising activated carbon in the shape of cylinders (mean diameter of 2 mm, mean length of 12 mm). The front-end pressure at the adsorber bed is 1.05 bar abs. The adsorber bed occupies a volume of 200 $cm^3$, the mass of the activated carbon is 100.0 g and the void volume is about 65%. The dimensions of the adsorber bed are: internal diameter 30 mm, length 300 mm.

At a volume flow of 200 standard ml/h of epoxysilane and thus a residence time of 39 minutes in the adsorber bed, a Pt content of 1 ppm is found in the eluate. The Pt content of the epoxysilane is thus reduced by 92%. According to GC analysis, the epoxysilane experiences no change over the adsorber bed.

As in Example 1, no further cyclized epoxysilane is formed during the subsequent batch distillation after the crude epoxysilane product has been purified by adsorption. After purification by adsorption, an epoxysilane purity of 99.5%. can be achieved in the separation by distillation, while without purification of the crude epoxysilane mixture by adsorption a purity of only 98.5% can be achieved in the work-up by distillation under the same boundary conditions.

Example 3

Crude GLYMO product having a Pt content of 3 ppm is passed at 120° C. over an absorber bed comprising granulated activated carbon (mean diameter of 1.5 mm). The front-end pressure at the absorber bed is 1.05 bar abs. The absorber bed occupies a volume of 100 cm3, the mass of the activated carbon is 48.1 g and the void volume is about 60%. The dimensions of the absorber bed are: internal diameter 20 mm, length 320 mm. At a volume flow of 80 standard ml/h of epoxysilane and a residence time of 45 minutes in the absorber bed, the Pt content of the eluate is below the detection limit of <1 ppm. Platinum is thus virtually completely removed. According to GC analysis, the epoxysilane experiences no change over the absorber bed.

As in Example 1, no further cyclized epoxysilane is formed during the subsequent batch distillation after the crude epoxysilane product has been purified by adsorption. After purification by adsorption, an epoxysilane purity of 99.5% can be achieved in the separation by distillation, while without purification of the crude epoxysilane mixture by adsorption a purity of only 98.5% can be achieved in the work-up by distillation under the same boundary conditions.

Example 4

400 g of the eluate from Example 3 having a cyclized epoxysilane content of 0.10% (corresponding to 0.4 g of cyclized epoxysilane) are freed of the low boilers (20%, corresponding to 80 g) in a batch distillation and held for 48 hours at 170° C. and a pressure of 63 mbar abs. under conditions of infinitely high reflux. After a time of 48 hours, the liquid phase was again analyzed by gas chromatography: the proportion of cyclized epoxysilane is then 0.125%, corresponding to 0.4 g. There has therefore been no further formation of the cyclized epoxysilane under the conditions of the distillation and in the absence of the homogeneous catalyst.

Example 5

400 g of the crude epoxysilane mixture from Example 3 which has not been subjected to the adsorption and has a cyclized epoxysilane content of 0.10% (corresponding to 0.4 g) are freed of the low boilers (20%, corresponding to 80 g), in a batch distillation and held for 48 hours at 170° C. and a pressure of 63 mbar abs. under conditions of infinitely high reflux. After a time of 48 hours, the liquid phase is again analyzed by gas chromatography: the proportion of cyclized epoxysilane is then 0.45%, corresponding to 1.44 g. Further formation of the cyclized epoxysilane has thus taken place under the conditions of the distillation in the presence of the homogeneous catalyst and the amount of cyclized epoxysilane has increased by a factor of 3.6 from 0.4 g to 1.44 g.

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 19934576.7, filed on Jul. 23, 1999, and incorporated herein by reference in its entirety.

What is claimed is:

1. A process for preparing a glycidyloxysilane, comprising:

reacting a hydrogensilane with an allyl glycidyl ether in the presence of a catalyst to form a crude product, then removing the catalyst from the crude product by reduction or by absorption with an absorber selected from the group consisting of activated carbon, silica, aluminum oxide, titanium oxide, zirconium oxide and a zeolite, and then distilling the crude product, whereby cyclization of the glycidyloxysilane is substantially obviated.

2. The process of claim 1, wherein the catalyst is removed from the crude product by absorption with said absorber.

3. The process of claim 2, wherein the adsorption is carried out in a fixed absorber bed.

4. The process of claim 2, wherein the absorber has a mean particle size of from 1 to 30 mm.

5. The process of claim 2, wherein the absorber has an internal surface area of from 10 to 1500 m$^2$/g.

6. The process of claim 2, wherein the absorber is an essentially water-free adsorbent.

7. The process of claim 2, wherein the adsorption is carried out at a temperature in the range from 0 to 120° C.

8. The process of claim 2, wherein the adsorption is carried out at a pressure in the range from 0.5 to 5 bar absolute.

9. The process of claim 3, wherein the residence time of the crude product in the absorber bed is from 5 minutes to 2 hours.

10. The process of claim 1, wherein removing the catalyst is accomplished by reducing the catalyst, wherein the reduced catalyst precipitates from the crude mixture.

11. The process of claim 10 wherein the reducing agent is metallic zinc.

12. The process of claim 1, wherein the glycidyloxysilane is represented by the formula I:

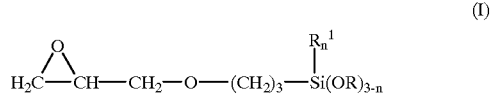

(I)

wherein

R is a linear or branched alkyl group having from 1 to 4 carbon atoms or an aryl group, R$^1$ is a linear or branched alkyl group having from 1 to 4 carbon atoms, and n is 0 or 1 or 2.

13. The process of claim 1, wherein the aryl group is a phenyl group.

14. The process of claim 1, wherein the catalyst comprises Pt, Pd, Rh or Ir.

15. The process of claim 1, wherein the glycidyloxysilane has a purity of ≧99%.

* * * * *